United States Patent [19]

Mignani et al.

[11] Patent Number: 4,594,460
[45] Date of Patent: Jun. 10, 1986

[54] PROCESS FOR SELECTIVE C-ALKYLATION OF PHENOLS

[75] Inventors: Geràrd Mignani, Lyons; Didier Morel, Villiers sur Orge, both of France

[73] Assignee: Rhone-Poulenc Sante, Courbevoie, France

[21] Appl. No.: 713,691

[22] Filed: Mar. 19, 1985

[30] Foreign Application Priority Data

Mar. 22, 1984 [FR] France .................. 84 04443

[51] Int. Cl.$^4$ ................ C07C 37/14; C07C 39/06
[52] U.S. Cl. .................... 568/794; 560/61; 560/67; 560/109; 560/144; 568/650; 568/706; 568/737; 568/744; 568/766; 568/780
[58] Field of Search .......... 568/794, 790, 780, 781, 568/789, 766, 785, 744, 745, 743, 736, 737, 706, 650, 651, 774; 560/66, 67, 144, 109

[56] References Cited

U.S. PATENT DOCUMENTS

| | | | |
|---|---|---|---|
| 3,518,318 | 6/1970 | Smutny | 568/766 |
| 4,163,864 | 8/1979 | Morita et al. | 568/651 |
| 4,168,271 | 9/1979 | Cardenes et al. | 260/345.5 |
| 4,400,545 | 8/1983 | Willis et al. | 568/377 |

FOREIGN PATENT DOCUMENTS

| | | | |
|---|---|---|---|
| 577710 | 6/1959 | Canada | 568/793 |
| 577711 | 6/1959 | Canada | 568/793 |
| 3122 | 12/1963 | Japan | 568/790 |
| 6135443 | 10/1981 | Japan | 560/61 |

OTHER PUBLICATIONS

Dewhirst et al., "J. Org. Chem." vol. 28, pp. 298–802, (1963).
Bader et al., "J. Amer. Chem. Soc." vol. 80, pp. 3073–3076 (1958).
Bolzonia et al., "Angew. Chem. Int. ed vol. 17(9) p. 684 (1978).
Ahluwala et al., "Tetrahedron" vol. 17, p. 1437 (1981).
Smutny, "Annals New York Academy of Science" pp. 125 and 126 (1973).

*Primary Examiner*—Werren B. Lone
*Attorney, Agent, or Firm*—Stevens, Davis, Miller & Mosher

[57] ABSTRACT

Substituted phenols of formula

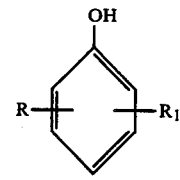
(I)

in which $R_1$ is in an ortho or para position relative to the phenol function and denotes

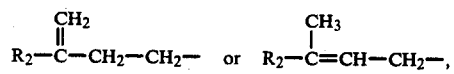

$R_2$ denotes an acyclic radical optionally substituted by alkyl, hydroxy, alkoxycarbonyl, cyano or formyl, or a phenyl or naphthyl radical, and R denotes hydrogen or 1 to 4 substituents chosen from halogen, OH optionally in the form of ether or ester, alkyl, $NO_2$, CHO optionally in the form of acetal, $CH_3CO—$, $C_6H_5CO—$, $NH_2$, alkylamino, dialkylamino or alkoxycarbonyl, it being understood that 2 symbols R may form with the phenyl nucleus a condensed aromatic ring, which comprises reacting a butadiene of formula

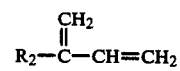
(II)

with a phenol for formula

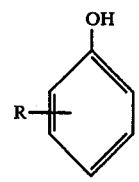
(III)

in water in the presence of a rhodium-based catalyst, a water-soluble phosphine and optionally an inorganic or organic base. The products of formula (I) are intermediates for the synthesis of vitamin E, antioxidants, perfumes or insecticides.

9 Claims, No Drawings

PROCESS FOR SELECTIVE C-ALKYLATION OF PHENOLS

The present invention relates to the preparation of substituted phenols of formula:

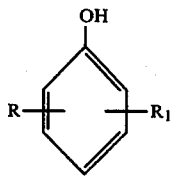
(I)

in which $R_1$ is in ortho or para position to the hydroxyl group and is a radical of formula:

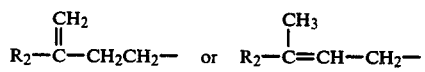

in which $R_2$ is an acyclic radical of 1 to 20 carbon atoms which is unsubstituted or substituted by one or more hydroxy, alkoxycarbonyl, cyano or formyl radicals, or a phenyl or naphthyl radical, which is unsubstituted or substituted by one or more alkyl radicals of 1 to 20 carbon atoms, and R is hydrogen or 1 to 4 substituents, which may be the same or different, chosen from halogen, hydroxy which may be in the form of an ether or ester, alkyl, nitro, formyl which may be in the form of an acetal, acetyl, benzoyl, amino, alkylamino, dialkylamino and alkoxycarbonyl, it being understood that two of the symbols R may form with the phenyl ring a condensed aromatic ring such as a naphthyl ring, by reaction of a butadiene of formula:

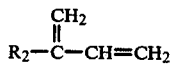
(II)

with a phenol of formula:

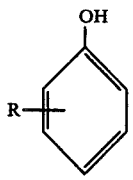
(III)

in which R is defined as before, and at least one position ortho or para to the hydroxy radical is unsubstituted.

Examples of acyclic radicals $R_2$ are the radicals of formulae $C_nH_{2n+1}$, $C_nH_{2n-1}$, $C_nH_{2n-3}$ and $C_nH_{n-1}$ where n is between 1 and 20, such as for example —$CH_3$ (in which case the butadiene of formula II is isoprene); —$C_2H_5$; —$C_4H_9$; —$C_8H_{17}$; —$C_{20}H_{41}$; —$C_4H_7$; —$C_6H_{11}$(myrcene); —$C_8H_{15}$; —$C_{10}H_{19}$; —$C_8H_{13}$; —$C_{11}H_{19}$($\beta$-farnesene); —$C_2H$, —$C_4H_3$; —$C_8H_7$, the common name of the most important compounds of formula (II) being shown in brackets.

Examples of optionally substituted phenyl and naphthyl radicals $R_2$ are the tolyl, xylyl, 8-methyl-1-naphthyl and 5,8-dimethyl-2-naphthyl radicals.

The alkylation of phenols with conjugated butadienes of formula (II) is a known reaction. However, the procedures described in the literature result in the formation of mixtures the components of which cannot be separated readily.

Thus, according to A. R. Bader and W. C. Bean, *J. Amer. Chem. Soc.*, 80, 3073 (1958), the reaction of phenol with isoprene, catalysed by 71% phosphoric acid at 20° C., produces a mixture of 6 products.

According to K. C. Dewhirst and F. F. Rust, *J. Org. Chem.*, 28, 798 (1963), treatment of phenol with isoprene in the presence of aluminium phenate at a low temperature produces a mixture of 4 products, the composition of which varies considerably with reaction conditions. It is impossible, moreover, to direct the reaction towards the formation of a single product.

According to L. Bolzoni et al., *Angew. Chem. Int.* Ed. 17 (9) 684 (1978), isoprene or myrcene reacts with phenol in the presence of potassium phenate and aluminium chloride to give chromanes. The use of phosphoric acid as a catalyst can also, according to V. K. Ahluwalia and K. K. Arora, *Tetrahedron* 17, 1437 (1981), result in the formation of chromanes.

U.S. Pat. No. 4,168,271 describes the condensation of phytatriene with trimethylhydroquinone in the presence of cuprous chloride and aluminium chloride in a mixture of benzene and ethyl acetate, which gives tocopherol in a yield of 47.2%.

It is also known, according to E. J. Smutny, *Ann. New York Acad. Sci.*, 125 (1973), to carry out the condensation of phenol with butadiene in the presence of palladium complexes. A mixture of ortho and para butenylphenols and butenyl phenyl ether is produced, in moderate yields (30 to 50%) and with a low degree of conversion (5 to 10%).

Lastly, according to the Japanese Patent Application published under no. 55/015,411, 3,4-dialkoxyphenols can be condensed with conjugated dienes, in particular isoprene, in the presence of a rhodium-based catalyst and a phosphine in an organic solvent, to produce 3,4-dialkoxyphenols C-alkylated in the ortho position.

A particular disadvantage of this liquid-phase alkylation process, in which the catalyst systems employed are homogeneous and in solution, lies in the fact that it is necessary to carry out a difficult additional treatment in order to separate the reaction products from the catalyst solution and to separate the catalyst to recycle it. For example, the catalyst may be recycled in the heavy residue obtained after the reaction products have been distilled off. Such treatment of the catalyst solution can be employed only when the reaction products are volatile, since the catalyst solutions decompose readily during the treatment, precipitating the metal in its metallic form. As a result, the catalyst system loses some of its efficiency, diminishing the industrial attractiveness of the process.

It is consequently desirable to have available an alkylation process which can be used in liquid phase in the presence of a rhodium-based catalyst, which makes it possible to overcome the disadvantages of the earlier processes, in particular where catalyst recovery is concerned, while retaining the advantages of the liquid-phase homogeneous catalysts which enable high yields and selectivities to be obtained.

It has now been found, and this is the subject of the present invention, that C-alkylation of a phenol of general formula (III) with a butadiene of general formula (II) can be carried out selectively by operating in water in the presence of a rhodium-based catalyst and a water-based phosphine, and optionally in the presence of a base, without an O-alkylation product being obtained.

The products obtained when the butadiene of formula (II) is isoprene or myrcene are of special interest.

The rhodium compound employed must be water-soluble or capable of dissolving in water under the reaction conditions via a coordination reaction with the water-soluble phosphine. The residue linked to the metal is not critical so long as it meets these conditions.

The rhodium derivative is generally an organic or inorganic salt of complex of rhodium, such as $RhCl_3$, $RhBr_3$, $Rh_2O$, $Rh_2O_3$, $Rh(NO_3)_3$, $Rh_2(CH_3COO)_4$, $Rh(CH_3COCHCOCH_3)_3$, $[RhCl(1,5-cyclooctadiene)]_2$, $[RhCl(CO_2]_2$ or $RhCl_3(C_2H_5NH_2)_3$. $RhCl_3$ and $[RhCl(1,5-cyclooctadiene)]_2$ are of particular interest.

The water-soluble phosphines which are particularly suitable are those described in French Patent FR 76/22,824, published under No. 2,366,237.

More particularly, at least one phosphine of general formula:

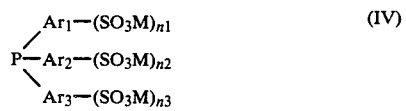

$$\begin{array}{c} Ar_1-(SO_3M)_{n1} \\ / \\ P-Ar_2-(SO_3M)_{n2} \\ \backslash \\ Ar_3-(SO_3M)_{n3} \end{array} \quad (IV)$$

is employed, in which $Ar_1$, $Ar_2$ and $Ar_3$, which are the same or different, each denote an optionally substituted phenylene or naphthylene radical, M is an inorganic or organic cation such that the phosphine of formula (IV) is soluble in water, and $n_1$, $n_2$ and $n_3$, which are identical or different, are integers from 0 to 3, at least one being greater than or equal to 1. The phenylene and naphthylene radicals may be substituted, for example, by one or more atoms or radicals chosen from halogen atoms and hydroxy, cyano, nitro, dialkylamino or alkoxycarbonyl radicals.

Preferably, in the phosphine of formula (IV), $Ar_1$, $Ar_2$ and $Ar_3$, which are identical or different, each denote an optionally substituted phenylene radical and at least one of the groups $SO_3M$ is in a meta position on the benzene ring.

M is preferably sodium, potassium, calcium, barium, ammonium or a quaternary ammonium cation such as tetrapropylammonium or tetrabutylammonium.

Preferably, $n_1$, $n_2$ and $n_3$ are 0 or 1, $n_1+n_2+n_3$ being from 1 to 3.

The phosphines of formula (IV) which can be employed in the process of the invention may be an alkali metal or alkaline-earth salt, an ammonium salt or a quaternary ammonium salt of (p-sulphophenyl)diphenylphosphine; (m-sulpho-p-methylphenyl)di(p-methylphenyl)phosphine; (m-sulpho-p-methoxyphenyl)di(p-methoxyphenyl)phosphine; (m-sulpho-p-chlorophenyl)di(p-chlorophenyl)phosphine; di(p-sulphophenyl)phenylphosphine; di(m-sulpho-p-methylphenyl)(p-methylphenyl)phosphine; di(m-sulpho-p-methoxyphenyl)(p-methoxyphenyl)phosphine; di(m-sulpho-p-chlorophenyl)(p-chlorophenyl)phosphine; tri(p-sulphophenyl)phosphine; tri(m-sulpho-p-methylphenyl)phosphine; tri(m-sulpho-p-methoxyphenyl)phosphine; tri(m-sulpho-p-chlorophenyl)phosphine; tri(o-sulpho-p-methylphenyl)phosphine; (o-sulpho-p-methylphenyl)(m-sulpho-p-methylphenyl)(m,m'-disulpho-p-methylphenyl)phosphine; or (m-sulphophenyl)(m-sulpho-p-chlorophenyl)(m,m'-disulpho-p-chlorophenyl)phosphine.

A quantity of rhodium or of a rhodium compound is used such that the number of gram-atoms of elementary rhodium per liter of reaction solution is from $10^{-4}$ to 1, preferably from $10^{-3}$ to 0.5.

The quantity of phosphine is chosen so that the number of gram-atoms of trivalent phosphorus relative to 1 gram-atom of rhodium is from 0.1 to 200, preferably from 3 to 100.

The minimum quantity of water required is that sufficient to dissolve all of the catalyst and at least a part of the starting materials of general formulae (II) and (III), the reaction taking place in aqueous phase and the reaction products being in a water-immiscible organic phase.

According to a particular but not obligatory embodiment of the invention, it is possible to operate in the presence of a cosolvent, in order to enhance the kinetics of the reaction and to be able to recycle the catalyst more easily.

More particularly, part of the water required to carry out the reaction may be replaced with an equivalent quantity of an aliphatic alcohol containing 1 to 4 carbon atoms, such as methanol, ethanol, isopropanol or butanol. The quantity of water which can be replaced is at most one half of the quantity of water required to carry out the reaction without a cosolvent.

To improve reactivity, a base may be added to the reaction mixture. Alkali metal or alkaline-earth hydroxides, carbonates and bicarbonates and aliphatic or aromatic tertiary amines may be mentioned as suitable bases. Generally, from 0.005 to 5 moles of base per liter of aqueous solution are employed.

In general, a slight molar excess of butadiene of formula (II) is employed relative to the phenol of general formula (III).

The reaction is generally carried out at a temperature below 200° C. and preferably between 50° and 125° C.

To make use of the process of the invention it is possible to charge either the catalyst solution prepared beforehand or the various components (phosphine, water, rhodium compound and the base if appropriate) into a suitable reactor, purged beforehand with an inert gas (nitrogen, argon). The reactor is heated to reaction temperature before or after the addition of the phenol which is itself added before or after, or at the same time as, the butadiene of general formula (II).

When the reaction is complete, the reactor is cooled to a temperature in the region of 20° C. The reactor contents are drained and the product of formula (I) is isolated from the organic phase by separation and, if need be, by extraction with a suitable solvent such as diethyl ether, pentane or hexane.

The product of formula (I) may be separated, for example, by distillation.

Uses for products of formula (I) may be found in various fields. In particular, suitably substituted products of formula (I) may be employed as intermediates in the synthesis of vitamin E or of antioxidants [G. W. Burton and K. U. Ingold, *J. Amer. Chem. Soc.*, 103, 6472 (1981)], perfumes (U.S. Pat. No. 4,400,545) or insecticides [P. Barua et al., *Tetrahedron Letters*, 24 (51) 5801 (1983)].

The following Examples show how the invention may be employed in practice.

EXAMPLE 1

In a 125 cc stainless steel autoclave are placed: $[RhCl(1,5-cyclooctadiene)]_2$ (0.0639 g, i.e. 0.26 milligram-atom of rhodium), tri(m-sulphophenyl)phosphine in sodium salt form (referred to hereafter as TPPTS Na)

(0.9246 g, i.e. 1.37 milligram-atom of P$^{3+}$) and sodium carbonate (0.2484 g; 2.3 mmol). The reactor is purged three times with argon and then distilled water (16 g), phenol (18.37 g; 0.195 mol) and isoprene (13.94 g; 0.205 mol) are added in succession. The mixture is heated to 100° C. and then stirred for 6 hours.

After cooling and separation, the organic phase is washed with water. In this manner, after drying over sodium sulphate, filtering and concentrating at 30° C. under reduced pressure (15 mm Hg; 2 kPa), an organic phase (6.31 g) is obtained, containing:
30% of 2-(3-methyl-3-butenyl)phenol
65% of 4-(3-methyl-3-butenyl)phenol and
5% of 3-(3-methyl-3-butenyl)phenol.
Isoprene conversion is 20%.

EXAMPLE 2

In a 125 cc stainless steel autoclave are placed: [RhCl(1,5-cyclooctadiene)]$_2$ (0.0302 g, i.e. 0.122 milligram-atom of rhodium), TPPTS Na (1 g, i.e. 1.48 milligram-atom of phosphorus) and sodium carbonate (0.025 g; 0.23 mmol). The autoclave is purged three times with argon and then distilled water (15 g), guaiacol (2-methoxyphenol) (12.4 g; 0.1 mol) and isoprene (7.02 g; 0.103 mol) are added in succession. The mixture is heated to 100° C. and then stirred for 6 hours.

After cooling and separation the organic phase is washed with water. After drying over sodium sulphate, filtering and concentrating, an organic phase (2.67 g) is obtained, containing:
72% of 4-(3-methyl-3-butenyl)-2-methoxyphenol
10% of 4-(3-methyl-2-butenyl)-2-methoxyphenol
14% of 6-(3-methyl-2-butenyl)-2-methoxyphenol
4% of 6-(3-methyl-2-butenyl)-2-methoxyphenol.
Isoprene conversion is 13.5%.

EXAMPLE 3

In a 125 cc stainless steel autoclave are placed: [RhCl(1,5-cyclooctadiene)]$_2$ (0.1 g, i.e. 0.406 milligram-atom of rhodium), TPPTS Na (1.6 g, i.e. 2.03 milligram-atom of phosphorus), sodium carbonate (0.252 g; 2.37 mmol) and pyrocatechol (8 g; 72.6 mmol). The autoclave is purged three times with argon and then distilled water (20 g) and isoprene (10.2 g; 0.15 mol) are added in succession. The mixture is heated to 100° C. and then stirred for 6 hours.

After cooling, separating and concentrating, an organic phase (13.94 g) is collected.

Isoprene conversion is 58% and that of pyrocatechol 100%.

Chromatographic analysis of the organic phase shows that the product obtained contains 68% of monoaddition products [3-(3-methyl-2-butenyl)-2-hydroxyphenol (40%) and 3-(3-methyl-3-butenyl)-2-hydroxyphenol (60%)] and 32% of diaddition product.

The structure of the products obtained is confirmed by the infrared spectrum, the proton nuclear magnetic resonance spectrum and the mass spectrum.

EXAMPLE 4

In a 125 cc stainless steel autoclave are placed: [RhCl(1,5-cyclooctadiene)]$_2$ (0.10 g, i.e. 0.406 milligram-atom of rhodium), TPPTS Na (1.6 g, i.e. 2.03 milligram-atom of phosphorus), sodium carbonate (0.252 g; 2.37 mmol) and hydroquinone (8 g; 72.6 mmol). The autoclave is purged three times with argon and then distilled water (20 g) and isoprene (5.44 g; 80 mmol) are added in succession. The mixture is heated to 100° C. and then stirred for 5 hours.

After cooling, separating and concentrating, an organic phase (11.83 g) is obtained.

Isoprene conversion is 70.4% and that of hydroquinone 57%.

Chromatographic analysis of the organic phase shows that the product obtained contains 82% of monoaddition products [2-(3-methyl-2-butenyl)hydroquinone (20%) and 2-(3-methyl-3-butenyl)hydroquinone (80%)] and 18% of diaddition product.

The structure of the products obtained is confirmed by the infrared spectrum, the proton nuclear magnetic resonance spectrum and the mass spectrum.

EXAMPLE 5

In a 125 cc stainless steel autoclave are placed: [RhCl(1,5-cyclooctadiene)]$_2$ (0.10 g, i.e. 0.406 milligram-atom of rhodium), TPPTS Na (1.6 g, i.e. 2.03 milligram atoms of phosphorus), sodium carbonate (0.252 g; 2.37 mmol) and trimethylhydroquinone (TMHQ) (5.616 g; 36.9 mmol). The autoclave is purged three times with argon and then distilled water (20 g) and isoprene (3.06 g; 45 mmol) are added in succession. The mixture is heated to 100° C. and then stirred for 6 hours.

After cooling, separating and concentrating, an organic phase (5.5 g) is collected, which crystallizes into a whitish solid.

Isoprene conversion is 14.7% and that of TMHQ 18%.

Chromatographic analysis of the solid obtained shows that it contains:
10% of 2-(3-methyl-2-butenyl)-3,5,6-trimethylhydroquinone,
80% of 2-(3-methyl-3butenyl)-3,5,6-trimethylhydroquinone and
10% of O-alkylated product.

The structure of the products obtained is confirmed by the infrared spectrum, the proton nuclear magnetic resonance spectrum and the mass spectrum.

EXAMPLE 6

In a 125 cc stainless steel autoclave are placed: [RhCl(1,5-cyclooctadiene)]$_2$ (0.10 g; 0.406 milligram-atom of rhodium), TPPTS Na (1.6 g; 2.56 milligram-atoms of P$^{3+}$), sodium carbonate (0.251 g; 2.36 mmol) and resorcinol (meta-hydroxyphenol) (8.02 g; 72.8 mmol). The autoclave is purged three times with argon and distilled water (20 g) and isoprene (5.44 g) are added. The mixture is heated at 100° C. for 6 hours.

After cooling, separating and concentrating at 30° C. under reduced pressure (15 mm Hg; 2 kPa), a yellow oily liquid (14.37 g) is collected.

Isoprene conversion is 100% and that of resorcinol 90.7%.

Chromatographic analysis of the oil shows the presence of 90% of monoaddition products [3-hydroxy(3-methyl-2-butenyl)phenol (45%) and 3-hydroxy(3-methyl-3-butenyl)phenol (55%)] and 10% of diaddition products.

The structure of the products obtained is confirmed by the proton nuclear magnetic resonance spectrum and the mass spectrum.

EXAMPLE 7

In a 125 cc stainless steel autoclave are placed: [RhCl(1,5-cyclooctadiene)]$_2$ (0.10 g; 0.406 milligraatom of rhodium), TPPTS Na (1.6 g; 2.56 milligram-atom of P$^{3+}$), sodium carbonate (0.251 g; 2.36 mmol) and 2-naphthol (10.54 g; 72.8 mmol). The autoclave is purged three times with argon and distilled water (20 g) and isoprene (5.44 g; 80 mmol) are added. The mixture is stirred at 100° C. for 16 hours.

After cooling, separating and concentrating at 30° C. under reduced pressure (15 mm Hg; 2 kPa), a beige-coloured solid (15.45 g) is collected.

Isoprene conversion is 88% and that of 2-naphthol 94%.

Chromatographic analysis of the solid shows the presence of 97% of monoaddition products [1-(3-methyl-3-butenyl)-2-naphthol (30%) and 1-(3-methyl-2-butenyl)naphthol (70%)] and 3% of diaddition products.

The structure of the products obtained is confirmed by the proton nuclear magnetic resonance spectrum and by the mass spectrum.

EXAMPLE 8

In a 125 cc stainless steel autoclave are placed: [RhCl(1,5-cyclooctadiene)]$_2$ (0.10 g; 0.406 milligram-atom of rhodium), TPPTS Na (1.23 g; 2 milligram-atoms of P$^{3+}$), sodium carbonate (0.251 g; 2.36 mmol) and para-cresol (7.96 g; 73.6 mmol). The autoclave is purged three times with argon and distilled water (20 g) and isoprene (5.44 g; 80 mmol) are added. The mixture is stirred at 100° C. for 16 hours.

After cooling, separating and concentrating at 30° C. under reduced pressure (15 mm Hg; 2 kPa), an orange oily liquid (10.07 g) is collected.

Isoprene conversion is 56% and that of para-cresol 60%.

Chromatographic analysis of the solid shows the presence of 98% of monoaddition products [4-methyl-2-(3-methyl-3-butenyl)phenol (80%) and 4-methyl-2-(3-methyl-2-butenyl)phenol (20%)] and 2% of diaddition products.

The structure of the products obtained is confirmed by the proton nuclear magnetic resonance spectrum and by the mass spectrum.

EXAMPLE 9

In a 125 cc stainless steel autoclave are placed: [RhCl(1,5-cyclooctadiene)]$_2$ (0.1 g; 0.406 milligram-atom of rhodium), TPPTS Na (1.23 g; 2 milligram-atoms of P$^{3+}$), sodium carbonate (0.251 g; 2.36 mmol) and 4-chlorophenol (9.77 g; 76 mmol). The autoclave is purged three times with argon and distilled water (20 g) and isoprene (5.44 g; 80 mmol) are added. The mixture is stirred at 100° C. for 16 hours.

After cooling, separating and concentrating at 30° C. under reduced pressure (15 mm Hg; 2 kPa), a red-brown oily liquid (11.01 g) is collected.

Isoprene conversion is 26.3% and that of 4-chlorophenol 21.3%.

Chromatographic analysis of the oil shows the presence of 100% of monoaddition products [4-chloro-2-(3-methyl-2-butenyl)phenol (17%) and 4-chloro-2-(3-methyl-3-butenyl)phenol (83%)].

The structure of the products obtained is confirmed by the proton nuclear magnetic resonance spectrum.

EXAMPLE 10

In a 125 cc stainless steel autoclave are placed: [RhCl(1,5-cyclooctadiene)]$_2$ (0.1 g; 0.406 milligram-atom of rhodium), TPPTS Na (1.23 g; 2 milligram-atoms of P$^{3+}$), sodium carbonate (0.251 g; 2.36 mmol) and methyl para-hydroxybenzoate (11.05 g; 72.6 mmol). The autoclave is purged three times with argon and distilled water (20 g) and isoprene (5.44 g; 80 mmol) are added. The mixture is stirred at 100° C. for 16 hours.

After cooling, separating and concentrating at 30° C. under reduced pressure (15 mm Hg; 2 kPa), a solid (10.06 g) is collected.

Isoprene conversion is 8.5% and that of methyl para-hydroxybenzoate 9.4%.

Chromatographic analysis of the solid shows the presence of 100% of monoaddition products [methyl 4-hydroxy-3-(3-methyl-2-butenyl)benzoate (33%) and methyl 4-hydroxy-3-(3-methyl-3-butenyl)benzoate (67%)].

The structure of the products obtained is confirmed by the proton nuclear magnetic resonance spectrum.

EXAMPLE 11

In a 125 cc stainless steel autoclave are placed: [RhCl(1,5-cyclooctadiene)]$_2$ (0.1 g; 0.406 milligram-atom of rhodium), TPPTS Na (1.23 g; 2 milligram-atoms of P$^{3+}$), sodium carbonate (0.251 g; 2.36 mmol) and 4-aminophenol (7.92 g; 72.55 mmol). The autoclave is purged three times with argon and distilled water (20 g) and isoprene (5.44 g; 80 mmol) are added. The mixture is stirred at 100° C. for 16 hours.

After cooling, separating and concentrating at 30° C. under reduced pressure (15 mm Hg; 2 kPa), a russet-coloured solid (11.86 g) is collected.

Isoprene conversion is 83.6% and that of 4-aminophenol 93%.

Chromatographic analysis shows the presence of 100% of monoaddition products [4-amino-2-(3-methyl-2-butenyl)phenol (40%) and 4-amino-2-(3-methyl-3-butenyl)phenol (60%)].

The structure of the products obtained is confirmed by the proton nuclear magnetic resonance spectrum.

EXAMPLE 12

In a 125 cc stainless steel autoclave are placed: [RhCl(1,5-cyclooctadiene)]$_2$ (0.1 g; 0.406 milligram-atom of rhodium), TPPTS Na (1.23 g; 2 milligram-atoms of P$^{3+}$) and sodium carbonate (0.251 g; 2.36 mmol). The autoclave is purged three times with argon and distilled water (20 g), 2-chlorophenol (9.33 g; 72.6 mmol) and isoprene (5.44 g; 80 mmol) are added. The mixture is stirred at 100° C. for 16 hours.

After cooling, separating and concentrating at 30° C. under reduced pressure (15 mm Hg; 2 kPa), a fluid yellow liquid (12.58 g) is collected.

Isoprene conversion is 76.6% and that of 2-chlorophenol 83.8%.

Chromatographic analysis shows the presence of 100% of monoaddition products [2-chloro-4-(3-methyl-2-butenyl)phenol (20%), 2-chloro-4-(3-methyl-3-butenyl)phenol (65), 2-chloro-6-(3-methyl-2-butenyl)phenol (5%) and 2-chloro-6-(3-methyl-3-butenyl)phenol (10%)].

The structure of the products obtained is confirmed by the proton nuclear magnetic resonance spectrum.

EXAMPLE 13

In a 125 cc stainless steel autoclave are placed: [RhCl(1,5-cyclooctadiene)]$_2$ (0.1 g; 0.406 milligram-atom of rhodium), TPPTS Na (1.23 g; 2 milligram-atoms of P$^{3+}$) and sodium carbonate (0.251 g; 2.36 mmol). The autoclave is purged three times with argon and distilled water (20 g), freshly distilled ortho-cresol (7.83 g; 72.4 mmol) and isoprene (5.44 g; 80 mmol) are added. The mixture is stirred at 100° C. for 16 hours.

After cooling, separating and concentrating at 30° C. under reduced pressure (15 mm Hg; 2 kPa), a fluid yellow liquid (12.71 g) is collected.

Isoprene conversion is 85.8% and that of orthocresol 92.9%.

Chromatographic analysis shows the presence of 100% of monoaddition products [2-methyl-4-(3-methyl-2-butenyl)phenol (10%), 2-methyl-4-(3-methyl-3-butenyl)phenol (70%) and 20% of a mixture of 2-methyl-6-(3-methyl-2-butenyl)phenol and 2-methyl-6-(3-methyl-3-butenyl)phenol].

The structure of the products obtained is confirmed by the proton nuclear magnetic resonance spectrum.

EXAMPLE 14

In a 125 cc stainless steel autoclave are placed: [RhCl(1,5-cyclooctadiene)]$_2$ (0.1 g; 0.406 milligram-atom of rhodium), TPPTS Na (1.23 g; 2 milligram-atoms of P$^{3+}$), sodium carbonate (0.25 g; 2.36 mmol) and 2-naphthol (10.8 g; 75 mmol). The autoclave is purged three times with argon and a 75/25 volume mixture of water and methanol (20 cc) and myrcene (10.9 g; 80 mmol) are added. The mixture is stirred at 100° C. for 24 hours.

After cooling, separating and concentrating at 30° C. under reduced pressure (15 mm Hg; 2 kPa) a yellow oil (11 g) is collected.

Myrcene conversion is 40% and that of 2-naphthol 65%.

Chromatographic analysis shows the presence of [1-(3,7-dimethyl-2,6-octadienyl)-2-naphthol (33%) and 1-(7-methyl-3-methylene-6-octenyl)-2-naphthol (67%)].

The structure of the products obtained is confirmed by the proton nuclear magnetic resonance spectrum and by the mass spectrum.

We claim:

1. A process for the preparation of a phenol of the formula:

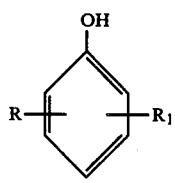

in which R$_1$ is in ortho or para position to the hydroxyl group and is a radical of formula

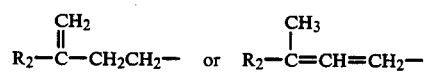

in which R$_2$ is an acyclic radical of 1 to 6 carbon atoms and R is hydrogen or 1 to 3 substituents, which may be the same or different, chosen from halogen, hydroxy which may be in the form of an ether, alkyl, amino, and alkoxycarbonyl, it being understood that two of the symbols R may form with the phenyl ring a condensed aromatic ring, which comprises reacting a butadiene of formula:

in which R$_2$ is defined as before, with a phenol of formula:

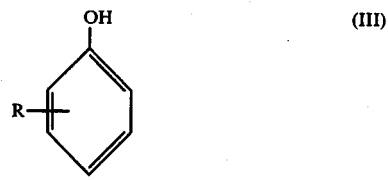

in which R is defined as before, and at least one position ortho or para to the hydroxy radical is unsubstituted, in sufficient water at a temperature from 50° C. to 200° C. to dissolve all the catalyst and at least a part of the phenol and substituted butadiene employed, in the presence of a rhodium-based catalyst in an amount from $10^{-4}$ to 1 gram-atoms of rhodium per liter of reaction solution, a water-soluble phosphine in an amount such that the number of gram-atoms of trivalent phosphorus relative to one gram-atom of rhodium is from 0.1 to 200, and an inorganic or organic base in an amount from 0.005 to 5 moles of base per liter of aqueous solution.

2. A process according to claim 1, in which the inorganic or organic base is an alkali metal or alkaline-earth metal hydroxide, carbonate or bicarbonate or an aliphatic or aromatic tertiary amine.

3. A process according to claim 1, in which the radical R$_2$ is an acyclic radical of formula $C_nH_{2n+1}$; $C_nH_{2n-1}$; $C_nH_{2n-3}$ or $C_nH_{2n-1}$ where n is an integer of from 1 to 6 inclusive.

4. A process according to claim 1, in which rhodium catalyst is an inorganic or organic rhodium salt or complex chosen from RhCl$_3$, RhBr$_3$, Rh$_2$O$_3$, Rh(NO$_3$)$_3$, Rh$_2$(CH$_3$COO)$_4$, Rh(CH$_3$COCHCOCH$_3$)$_3$, [RhCl(1,5-cyclooctadiene)]$_2$, [RhCl(CO)$_2$]$_2$, and RhCl$_3$(C$_2$H$_5$NH$_2$)$_3$.

5. A process according to claim 4, in which the rhodium catalyst is RhCl$_3$ or [RhCl(1,5-cyclooctadiene)]$_2$.

6. A process according to claim 1, in which the water-soluble phosphine has the formula:

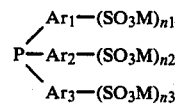

in which Ar$_1$, Ar$_2$ and Ar$_3$, which are the same or different, each denote unsubstituted or substituted phenylene or naphthylene, M is an inorganic or organic cation chosen from sodium, potassium, calcium, barium, ammonium and quaternary ammonium cations, and n$_1$, n$_2$ and n$_3$, which are the same or different, are each integers from 0 to 3, at least one being greater than 0.

7. A process according to claim 6, in which the water-soluble phosphine is the sodium salt of tri(m-sulphophenyl)phosphine.

8. A process according to claim 1, in which the operation is carried out in the presence of an aliphatic alcohol of 1 to 4 carbon atoms as cosolvent.

9. A process according to claim 8, in which the quantity of aliphatic alcohol employed is such as to replace at most one half of the quantity of water required for the use of the process without the cosolvent.

* * * * *